(12) United States Patent
Tsugawa et al.

(10) Patent No.: US 9,617,576 B2
(45) Date of Patent: Apr. 11, 2017

(54) ENZYME ELECTRODE

(75) Inventors: Wakako Tsugawa, Koganei (JP); Koji Sode, Tokyo (JP)

(73) Assignees: BIOENGINEERING LABORATORIES, LLC, Shinjuku-ku, Tokyo (JP); ARKRAY, INC., Kyoto-shi, Kyoto (JP); ULTIZYME INTERNATIONAL LTD., Meguro-ku, Tokyo (JP)

(*) Notice: Subject to any disclaimer, the term of this patent is extended or adjusted under 35 U.S.C. 154(b) by 355 days.

(21) Appl. No.: 12/678,268

(22) PCT Filed: Sep. 18, 2008

(86) PCT No.: PCT/JP2008/002573
§ 371 (c)(1),
(2), (4) Date: Mar. 15, 2010

(87) PCT Pub. No.: WO2009/037838
PCT Pub. Date: Mar. 26, 2009

(65) Prior Publication Data
US 2010/0261072 A1    Oct. 14, 2010

(30) Foreign Application Priority Data

Sep. 18, 2007  (JP) ................................. 2007-240812
May 12, 2008   (JP) ................................. 2008-124741

(51) Int. Cl.
*G01N 27/26* (2006.01)
*C12Q 1/00* (2006.01)
*C12Q 1/32* (2006.01)

(52) U.S. Cl.
CPC ............. *C12Q 1/001* (2013.01); *C12Q 1/006* (2013.01); *C12Q 1/32* (2013.01)

(58) Field of Classification Search
CPC ........... C12Q 1/001; C12Q 1/32; C12Q 1/006
(Continued)

(56) References Cited

U.S. PATENT DOCUMENTS 3,669,864 A * 6/1972 Fike .............................. 204/412
4,220,615 A * 9/1980 Sommarlund ................ 264/104
(Continued)

FOREIGN PATENT DOCUMENTS

EP   1 661 516      5/2006
JP   01-503409     11/1989
(Continued)

OTHER PUBLICATIONS

Furuya et al, Ag Loaded Gas Diffusion Electrodes for Chlor-Alkali Electrolysis, pp. 89-96, 1998, Energy and Electrochemical Processing for a Cleaner Environment.*
(Continued)

*Primary Examiner* — Matthew Martin
*Assistant Examiner* — Kourtney S Carlson
(74) *Attorney, Agent, or Firm* — Knobbe, Martens, Olson & Bear LLP

(57) ABSTRACT

The present invention provides an enzyme electrode composed of a carbon particle on which glucose dehydrogenase (GDH) with flavine adenine dinucleotide (FAD) as a coenzyme is supported and an electrode layer contacting the carbon particle, wherein the carbon particle and/or the electrode layer are/is composed of the carbon particles with a particle diameter of not more than 100 nm and a specific surface area of at least 200 $m^2/g$.

11 Claims, 8 Drawing Sheets

(58) Field of Classification Search
USPC ......... 204/403.01, 403.14; 429/401; 427/541
See application file for complete search history.

(56) References Cited

U.S. PATENT DOCUMENTS

| | | | |
|---|---|---|---|
| 4,970,145 A * | 11/1990 | Bennetto | C12Q 1/002 |
| | | | 204/403.11 |
| 5,122,456 A | 6/1992 | Bennetto et al. | |
| 5,160,418 A * | 11/1992 | Mullen | C12Q 1/005 |
| | | | 204/403.14 |
| 5,755,953 A * | 5/1998 | Henning et al. | 205/778 |
| 6,475,372 B1 | 11/2002 | Ohara et al. | |
| 6,977,180 B2 | 12/2005 | Hellinga et al. | |
| 7,638,228 B2 * | 12/2009 | Minteer et al. | 429/401 |
| 2003/0129622 A1 | 7/2003 | Hellinga et al. | |
| 2012/0037514 A1 | 2/2012 | Wu et al. | |

FOREIGN PATENT DOCUMENTS

| | | |
|---|---|---|
| JP | 2005-502045 | 1/2005 |
| JP | 2007-509355 | 4/2007 |
| JP | 2007-218795 | 8/2007 |
| RU | 2 262 890 | 10/2005 |
| WO | WO 88/08446 | 11/1988 |
| WO | WO 2005/093400 | 10/2005 |
| WO | WO 2005/121355 | 12/2005 |
| WO | WO 2007/055100 | 5/2007 |

OTHER PUBLICATIONS

Translation of INOSE et al WO 2007/055100.*
"Tanaka Precious Metals—Pt and Pt Ru Alloy/Carbon Catalysts for PEFCs." Dec. 1, 2012. <http://pro.tanaka.co.jp/en/products/group_f/f_4.html>.*
Pantea et al (Pantea, Dana, Hans Darmstadt, Serge Kaliaguine, and Christian Roy. "Electrical Conductivity of Conductive Carbon Blacks: Influence of Surface Chemistry and Topology." Applied Surface Science 217.1-4 (2003): 181-93.).*
Bremle, Gudrun, Björn Persson, and Lo Gorton. "An Amperometric Glucose Electrode Based on Carbon Paste, Chemically Modified with Glucose Dehydrogenase, Nicotinamide Adenine Dinucleotide, and a Phenoxazine Mediator, Coated with a Poly(ester Sulfonic Acid) Cation Exchanger." Electroanalysis 3.2 (1991): 77-86.*
Tsujimura, Seiya, Shinki Kojima, Kenji Kano, Tokuji Ikeda, Mika Sato, Hirokazu Sanada, and Hironori Omura. "Novel FAD-Dependent Glucose Dehydrogenase for a Dioxygen-Insensitive Glucose Biosensor." Bioscience, Biotechnology, and Biochemistry 70.3 (2006): 654-59.*
Palleschi, et al. "Studies of Amperometric Glucose Dehydrogenase Electrodes for Glucose," *Analytica Chimica Acta*, vol. 192, No. 2, pp. 339-343, 1987.
Supplementary European Search Report mailed on Aug. 4, 2010 and issued to European patent application EP 08 83 2471.
Kamitaka, et al. "High Current Density Bioelectrolysis of D-Fructose at Fructose Dehydrogenase-Adsorbed and Ketjen Black-modified Electrodes Without a Mediator," *Chemistry Letters*, vol. 36, No. 2, pp. 218-219, 2007.
Tsujimura, et al. "CueO-immobilized Porous Carbon Electrode Exhibiting Improved Performance of Electrochemical Reduction of Dioxygen to Water," *Electrochimica Acta*, vol. 53, pp. 5716-5720, 2008.
Tsutsumi, et al. "Direct Electrochemistry of Histamine Dehydrogenase from *Nocardioides simplex*," *Journal of Electroanalytical Chemistry*, vol. 625, pp. 144-148, 2009.
International Search Report dated Oct. 28, 2008 and issued to the priority international application No. PCT/JP2008/002573.
Decision of Grant issued to corresponding Russian patent application No. 2010115275.
Office Action dated Aug. 7, 2012 issued to corresponding Japanese patent application No. 2009-533048.
Final Decision of Rejection dated Dec. 4, 2012 issued to corresponding Japanese Application No. 2009-533048.
Office Action issued in corresponding Indian Patent Application No. 1504/CHENP/2010, on May 16, 2014.
Cabot Material Safety Data Sheet, Prepared in accordance with ISO 11014-1/ ANSI standard Z400.1-2004, Cabot Corporation—Safety, Health and Environmental Affairs, in 13 pages (Dec. 4, 2012).
Das et al., "Electrical and Mechanical Properties of Conductive Carbon Black Filled EVA, EPDM and their Blends", Raw Materials and Applications, *KGK Kautschuk Gummi Kunststoffe*, vol. 55(6), pp. 300-306 (2002).
Middaugh, "How to Make Cathodes with a Diffusion Layer for Single-Chamber Microbial Fuel Cells," in 7 pages (Jun. 5, 2006).
Office Action issued in corresponding European Patent Application No. 13186241.9, on Jun. 19, 2014.
Office Action issued in European Patent Application No. 13186241.9 on Oct. 24, 2014.
Office Action issued in Canadian Patent Application No. 2,699,823, on Jan. 27, 2015.
White et al., "Investigations of Platinized and Rhodinized Carbon Electrodes for Use in Glucose Sensors," *Electroanalysis*, vol. 6, pp. 625-632 (1994).
Akiyoshi et al., "Catalytic Activities of Supported Transition Metals for Decomposition of Methanol to CO and $H_2$," *Sekiyu Gakkaishi*, vol. 30(3), pp. 156-160 (1987).
He et al., "Application of Bacterial Biocathodes in Microbial Fuel Cells," *Electroanalysis*, vol. 18(19-20), pp. 2009-2015 (2006).

* cited by examiner

ENZYME ELECTRODE

CROSS-REFERENCE TO RELATED APPLICATIONS

This application is the U.S. National Phase under 35 U.S.C. §371 of International Application PCT/JP2008/002573, filed Sep. 18, 2008, which was published in a non-English language, which claims priority to JP 2007-240812, filed Sep. 18, 2007 and JP 2008-124741, filed May 12, 2008.

TECHNICAL FIELD

The present invention relates to an enzyme electrode on which an ink containing glucose dehydrogenase is supported, in particular, an enzyme electrode used as a glucose sensor, an ink used for producing the enzyme electrode, and a method for producing the enzyme electrode.

BACKGROUND ART

An enzyme electrode usually refers to an electrode in which an enzyme is fixed on the surface of an electrode such as a gold electrode, platinum electrode or carbon electrode. Taking advantage of the reaction specificity of the enzyme, the enzyme electrode has been widely used as a biosensor to specifically detect various physiologically active substances. In particular, the enzyme electrode can be used as a glucose sensor for measuring the concentration of glucose in blood as an important marker in diabetes.

Examples of oxidoreductases used for an enzyme electrode include dehydrogenases represented by glucose dehydrogenase (GDH) and oxidases represented by glucose oxidase (GOD). GOD has a high substrate specificity to glucose and is excellent in heat stability. Since mass production of this enzyme is possible, its production cost is lower than other enzymes, which is advantageous. Also, a system using GDH is unlikely to be influenced by oxygen dissolved in a measurement sample. Therefore, even when the measurement is carried under conditions of low oxygen partial pressure or even when the measurement is carried out for a high concentration of sample requiring a large amount of the enzyme, glucose can be precisely measured.

In cases where these oxidoreductases are applied to the enzyme electrode, there has been a problem that a response current value of the electrode is low. Therefore, the inventors of the present invention proposed, in order to improve the response current value of the electrode, an enzyme electrode having an electron transfer protein together with an electron mediator (see Patent Document 2 below).

The electron mediator refers a redox substance such as a non-protein metal complex or an organic compound, the substance being capable of mediating electron transfer from an oxidoreductase to an electrode. Examples thereof include potassium ferricyanide, phenazine methosulfate, ferrocene and derivatives thereof.

The electron transfer protein refers to a protein capable of being reduced by receiving electrons from an electron donor and then oxidized by donating the electrons to an electron acceptor in an oxidation-reduction system in the body. Examples of the electron transfer protein include cytochrome b and cytochrome C, and preferably cytochrome b562 or the like.

In Patent Document 1, an electron transfer protein, together with oxidoreductase, is immobilized on an electrode and thus electron transfer from a the oxidoreductase to the electrode or to an electron mediator can be promoted, thereby obtaining an enzyme electrode with a high response current value.

For the measurement of the concentration of glucose using these enzyme electrodes, in general, a buffer is put into a thermostat cell, and a coenzyme, $CaCl_2$ and the electron mediator are added thereto. The mixture is then kept at a constant temperature. Thereafter, as a working electrode, for example, an enzyme electrode in which an enzyme is immobilized on a carbon electrode is used. And a counter electrode (for example, platinum electrode) and a reference electrode (for example, Ag/AgCl electrode) are used. A constant voltage is applied to the above-mentioned carbon electrode and after an electric current reaches a steady state, a sample containing glucose is added and then an increase in the electric current is measured.

Thus, these conventional methods require the electron mediator to be included in the electrode, to be immobilized on the surface of the electrode, or to be added into the thermostat cell as an aqueous solution. And, the electron mediator needs to be provided separately from the oxidoreductase. Therefore, the process was complicated and there were problems in the cost of mass production.

Patent Document 1: JP 2003-121407 A
Patent Document 2: WO 02/73181
Patent Document 3: WO 2005/023111

DISCLOSURE OF THE INVENTION

Problems to be Solved by the Invention

An object of the present invention is to provide an enzyme electrode, which does not require an electron mediator to be used and is not inferior to those using the electron mediator, allowing a high response current value to be obtained and a wide dynamic range to be obtained particularly when used as a glucose sensor.

Means for Solving the Problems

In the present invention, it has been found that, when an enzyme electrode composed of carbon particles on which glucose dehydrogenase is supported and an electrode layer contacting the above-mentioned carbon particles is used as a sensor for measuring glucose, wherein the particle diameter of the above-mentioned carbon particle and/or the carbon particle composing the above-mentioned electrode layer is not more than 100 nm and the specific surface area thereof is at least 200 $m^2/g$, electrons smoothly transfers between the above-mentioned electrode layer and carbon particles supporting glucose dehydrogenase, or between the carbon particles composing the electrode layer and carbon particles supporting glucose dehydrogenase, and thus the function as the enzyme electrode can be attained Hence, the present invention enables a response current to be enhanced in the enzyme electrode as composed above, by adjusting the particle diameter and specific surface area of the carbon particle on which glucose dehydrogenase is supported, regardless of the form or size of an electrode material contacting the carbon particle on which glucose dehydrogenase is supported.

Also, the present invention enables the response current to be further enhanced in the enzyme electrode as composed above, by using the carbon particles as the electron material contacting the carbon particles on which glucose dehydrogenase is supported, as well as by adjusting their particle diameter and specific surface area.

The concrete structure of the present invention is as follows:

(1) An enzyme electrode comprising carbon particles carrying glucose dehydrogenase (GDH) with flavine adenine dinucleotide (FAD) as a coenzyme; and an electrode layer contacting said carbon particles, wherein the carbon particles and/or the electrode layer are/is composed of carbon particles with a particle diameter of not more than 100 nm and a specific surface area of at least 200 m$^2$/g.

(2) The enzyme electrode according to (1), wherein the glucose dehydrogenase (GDH) is an oxidoreductase catalytic subunit or a complex of an oxidoreductase catalytic subunit and an electron transfer subunit.

(3) The enzyme electrode according to (1) or (2), wherein the electrode layer is composed of metal.

(4) The enzyme electrode according to (3), wherein the electrode layer is composed of metal wire.

(5) The enzyme electrode according to any one of (1) to (4), which is used as a glucose sensor.

(6) An ink material to be used for an enzyme electrode comprising glucose dehydrogenase (GDH) with flavine adenine dinucleotide (FAD) as a coenzyme; and carbon particles having a diameter of not more than 100 nm and a specific surface area of at least 200 m$^2$/g.

(7) The ink material according to (6), wherein the glucose dehydrogenase (GDH) is an oxidoreductase catalytic subunit or a complex of an oxidoreductase catalytic subunit and an electron transfer subunit.

(8) A method for producing an enzyme electrode, comprising coating a surface of an electrode layer with the ink material according to (6) or (7) and then drying.

The carbon particle used in the present invention on which glucose dehydrogenase (GDH) with flavine adenine dinucleotide (FAD) as a coenzyme is supported is characterized by its small particle diameter and large specific surface area. The carbon particle having a particle diameter of not more than 100 nm and a specific surface area of at least 200 m$^2$/g is preferred, and a particle diameter of not more than 50 nm and a specific surface area of at least 200 m$^2$/g is more preferred. Examples of such a carbon particle include commercially available Ketchen black (particle diameter 34 nm, specific surface area 1400 m$^2$/g), VULCAN (particle diameter 30 nm, specific surface area 254 m$^2$/g) and Lion Paste (a trademark of Lion Corporation) containing Ketchen black.

In the present invention, the above-mentioned carbon particles are mixed together with glucose dehydrogenase using flavine adenine dinucleotide (FAD) as a coenzyme (in the present specification, referred to as "FADGDH") to prepare an ink material which composes an enzyme electrode. The ink material can be produced by adding a solvent, for example, a propanol aqueous solution to the carbon particles, for example, Ketchen black and mixing the mixture well.

In the present invention, the enzyme electrode is, in general, produced by coating an electrode layer with the above-mentioned ink material.

For the electrode layer used in the present invention, the carbon particle or a metal can be used. The carbon particle whose particle diameter is small and whose specific surface area is large is preferred, but not particularly limited. More preferably, the carbon particle has a particle diameter of not more than 100 nm, still more preferably a particle diameter of not more than 50 nm, and a specific surface area of at least 200 m$^2$/g. Examples of such a carbon particle include commercially available Ketchen black (particle diameter 34 nm, specific surface area 1400 m$^2$/g), VULCAN (particle diameter 30 nm, specific surface area 254 m$^2$/g) and Lion Paste (a trademark of Lion Corporation) containing Ketchen black. In cases where the metal is used, it is preferred to use a metal wire, more preferably a gold wire or stainless wire.

Glucose dehydrogenase used in the present invention may be a modified oxidoreductase in which part of natural oxidoreductase is chemically modified. Such a modified enzyme can be produced by, for example, replacing one or more amino acid residues of the protein with other naturally-occurring or not naturally-occurring amino acid residues, or deleting or adding one or more amino acids.

As described above, the enzyme electrode according to the present invention does not require the electron mediator in the transfer of electrons to the electrode layer by adjusting the particle diameter and specific surface area of the carbon particle on which glucose dehydrogenase is supported. The glucose dehydrogenase used in the present invention is, from the viewpoint of functions, composed of a catalytically active subunit having a glucose dehydrogenation activity and an electron transfer subunit comprising an electron transfer protein for conferring electrons provided from the above-mentioned catalytic subunit to the electrode layer. In this case, in the present invention, the catalytic subunit alone may be used as oxidoreductase, or a complex of the catalytic subunit and the electron transfer subunit may be used.

The catalytic subunit has functions of taking an electron out of glucose in a sample and donating this electron to the electron transfer subunit. Preferably, the FADGDH catalytic subunit with flavine adenine dinucleotide (FAD) as a coenzyme is used. Therefore, to the electron transfer subunit, the electron is provided from the catalytic subunit via a reduced FAD.

The content of the catalytic subunit is, for example, set an amount corresponding to 5 to 100 U in terms of activity. Here, the definition of enzyme 1 unit (1 U) is known for each enzyme. For example, in the case of GDH, when decoloration based on reduction of DCIP (2,6-dichloroindophenol) under standard test conditions (pH 6.0, 37° C.) is measured with time at an absorption wavelength of 600 nm, which is absorption wavelength of DCIP, 1 unit is defined as the amount of the enzyme which oxidizes 1 µM glucose every 1 minute (molar extinction coefficient is 4.76×1000 µM/cm).

FADGDH is not particularly limited, as long as it is a catalytic subunit having a glucose dehydrogenation activity or an FADGDH complex in which an electron transfer subunit is bound to the above-mentioned catalytic subunit. Among them, it is preferred to use *Burkholderia cepacia*, in particular, *Burkholderia cepacia* KS1 strain (in this specification, referred to as "KS1 strain").

The KS1 strain is a novel strain isolated from soil in the vicinity of a hot spring and identified as *Burkholderia cepacia* based on its mycological properties. It has been deposited with International Patent Organism Depositary, National Institute of Advanced Industrial Science and Technology (AIST Tsukuba Central 6, 1-1-1 Higashi, Tsukuba, Ibaraki, Japan, 305-8566), under accession No. FERM BP-7306 since Sep. 25, 2000. Details of the KS1 strain are disclosed in WO 02/36779. It can produce GDH containing the α subunit (molecular weight of about 60 kDa) which is a catalytic subunit, the β subunit (molecular weight of about 43 kDa) corresponding to cytochrome c which is an electron transfer subunit and the γ subunit (molecular weight of about 14 kDa). The molecular weight was measured by SDS-polyacrylamide gel electrophoresis under reduction conditions.

In order to produce the enzyme electrode according to the present invention, glucose dehydrogenase or a complex thereof is mixed well together with carbon powders and the resultant is mounted on the electrode. In order to immobilize glucose dehydrogenase or the complex thereof onto the carbon particle, after the mounting on the electrode as describe above, for example, a cross-linking treatment is performed using a binary cross-linking reagent such as glutaraldehyde. Alternatively, immobilization using a solid polyelectrolyte can also be carried out. It is Nafion that is used most as the solid polyelectrolyte. An enzyme immobilized film can be made by dissolving the solid polyelectrolyte including Nafion in a solvent such as isopropanol and adding this mixture dropwise to an enzyme film in which an enzyme is absorbed, or coated and dried; or mixing the Nafion solution with the enzyme and drying.

The enzyme electrode according to the present invention, in principle, operates without an electron mediator. However, use of the electron mediator is not ruled out. In cases where the electron mediator is used, it is not particularly limited and, for example, potassium ferricyanide, phenazine methosulfate, ruthenium complexes or the like can be used.

In cases where the enzyme electrode according to the present invention is used as a glucose sensor, the above-mentioned enzyme electrode is used as a working electrode. As a counter electrode, for example, a platinum electrode can be used and as a reference electrode, for example, an Ag/AgCl electrode can be used. A buffer is put into a thermostat cell and these electrodes are set. A constant voltage is then applied to the working electrode and after an electric current reaches a steady state, a sample containing glucose is added to the thermostat cell and an increase in the electric current is measured. In accordance with a calibration curve prepared from a glucose solution of standard concentrations, the glucose concentration in a sample can be calculated.

In addition, when used as the glucose sensor, the enzyme electrode can be composed such that, for example, the glucose concentration can be continuously measured and several glucose measurements can be carried out without interruption. In this case, the glucose sensor further comprises a collecting element for collecting blood or interstitial fluid from subcutaneous tissues and is composed such that the blood or interstitial fluid collected by the collecting element is allowed to contact the electrode.

The above-mentioned glucose sensor can be composed such that at least a portion of the electrode is embedded in the subcutaneous tissues and is used. In this case, the electrode is formed on an insulating substrate.

The enzyme electrode according to the present invention can be used as the anode of an enzyme fuel cell. In this case, a substrate according to the substrate specificity of the enzyme can be used as a fuel. For the cathode, a platinum supporting carbon electrode, a platinum electrode or the like can be used and an enzyme fuel cell without a partition wall can be constructed. As a reaction solution, a common buffer such as a phosphate buffer can be used. It can further be used in body fluids. An electromotive force can be adjusted by changing a resistance value applying to an external circuit.

BEST MODE FOR CARRYING OUT THE INVENTION

The present invention will now be described in detail by way of examples; however the present invention is not limited thereto.

Examples in the Case of Using Carbon Particle as Electrode Layer

First, the examples in cases where carbon particles are used for both an electrode layer and an enzyme layer are shown.

Example 1

Figure 1:
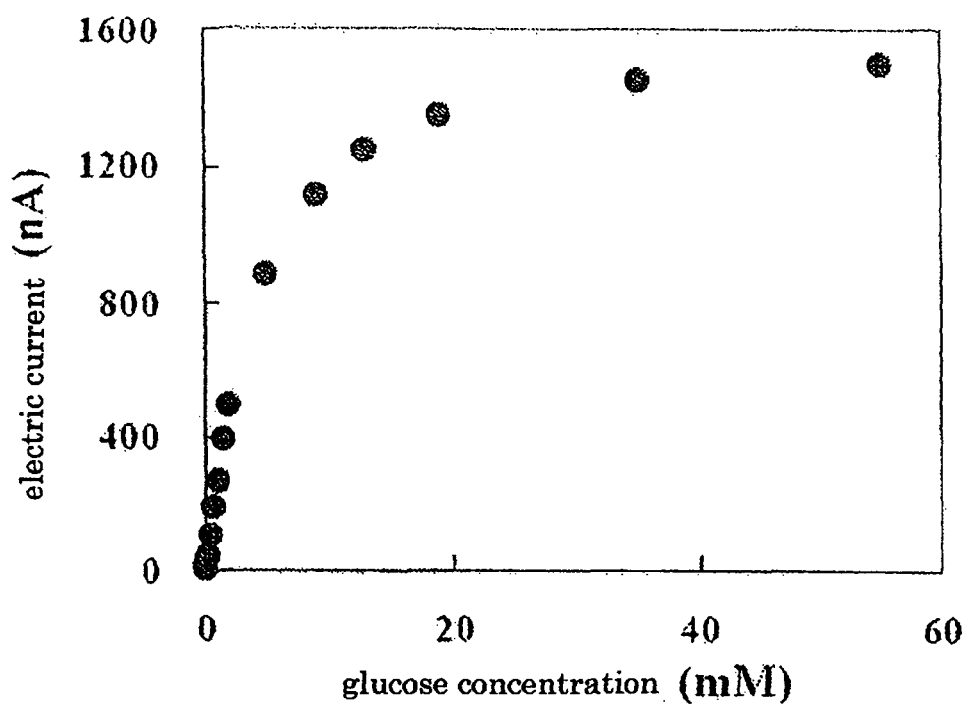
FIG. 1 shows the correlation between the glucose concentration and the electric current value when Ketchen black was used in the FADGDH enzyme immobilized layer and Ketchen black was used in the electrode layer.

Ketchen black (hereinafter referred to as KB) with a particle diameter of 34 nm, a specific surface area of 1400 m²/g and a porosity of 78 vol % is provided as a carbon particle. To KB (100 mg), Milli Q water (400 μl) and 5% Nafion (1-propanol 48% aqueous solution) (1 ml) were added. The mixture was mixed well and left to stand for 3 days to provide a KB ink. A mixture of 100 mM p.p.b. (pH 7.0) (10 μl) and 8.4 U/ml FADGDH (40 μl) with the KB ink (10 μl) was used as an FADGDH/KB ink. To an integral electrode (φ0.4 mm) filled with KB as an electrode material, the FADGDH/KB ink was added dropwise so as to obtain 25 U/mm² and dried at 4° C. for 2 hours. The prepared enzyme electrode was used as a working electrode, Pt was used as a counter electrode and an Ag/AgCl reference electrode was used as a reference electrode. FIG. 1 shows the results of measurements of a response current value upon addition of glucose when an electric potential was applied at +250 mV vs. Ag/AgCl using 100 mM p.p.b. (pH 7.0) (10 ml) as a reaction solution in a three electrode system. The measurement was carried out at 37° C. while the reaction solution was being stirred at 250 rpm. The response current value was defined as the difference obtained by subtracting the electric current value obtained at 0 mM glucose from the value measured at each glucose concentration.

As shown in FIG. 1, by gradually increasing the glucose concentration, the observed electric current value increased. At a final glucose concentration of 55 mM, the response current value was about 1500 nA. At 5 mM glucose, the current density was 6998 nA/mm². It was confirmed that, when the KB carbon particle with a particle diameter of not more than 100 nm and a specific surface area of at least 200 m²/g was used, a sufficient response current value was obtained.

Comparative Example 1

Figure 2:
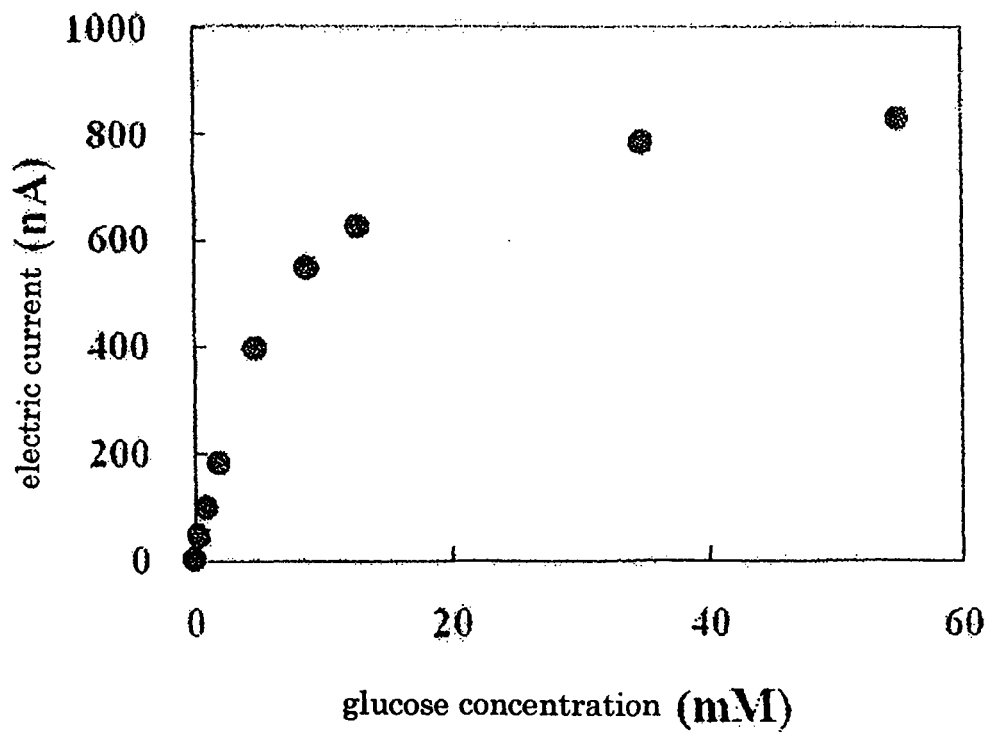
FIG. 2 shows the correlation between the glucose concentration and the electric current value when the carbon paste was used in the FADGDH enzyme immobilized layer and Ketchen black was used in the electrode material.

An enzyme electrode was prepared in the same procedures as described in Example 1 except that CP having a particle diameter of 7000 nm and a specific surface area of 1 m²/g, instead of KB, was used as a carbon particle. That is, to CP (100 mg), Milli Q water (400 μl) and 5% Nafion (1-propanol 48% aqueous solution) (1 ml) were added. The mixture was mixed well and left to stand for 3 days to provide a CP ink. A mixture of 100 mM p.p.b. (pH 7.0) (10 μl) and 8.4 U/ml FADGDH (40 μl) with the CP ink (10 μl) was used as an FADGDH/CP ink. To an integral electrode (φ0.4 mm) filled with KB as an electrode material, the FADGDH/CP ink was added dropwise so as to obtain 25 U/mm² and dried at 4° C. for 2 hours. The prepared enzyme electrode was used as a working electrode, Pt was used as a counter electrode and an Ag/AgCl reference electrode was used as a reference electrode. FIG. 2 shows the results of measurements of a response current value upon addition of glucose when an electric potential was applied at +250 mV vs. Ag/AgCl using 100 mM p.p.b. (pH 7.0) (10 ml) as a reaction solution in a three electrode system. The measurement was carried out at 37° C. while the reaction solution was being stirred at 250 rpm. The response current value was defined as the difference obtained by subtracting the electric current value obtained at 0 mM glucose from the value measured at each glucose concentration.

As shown in FIG. 2, by gradually increasing the glucose concentration, the observed electric current value increased. At a final glucose concentration of 55 mM, the response current value was about 800 nA. At 5 mM glucose, the current density was 3160 nA/mm². It was confirmed that, by comparing FIG. 1 and FIG. 2, in cases where the integral electrode filled with the same KB as an electrode layer was used, the response current value decreased from 1500 nA to about 800 nA by changing the ink material, with which this electrode was coated, from the FADGDH/KB ink to the FADGDH/CP ink. That is, it was confirmed that, when the same electrode layer was used, the smaller the particle diameter of the carbon particle on which the enzyme was supported was and the larger the specific surface area thereof was, the higher the respond current became.

Example 2

Figure 3:
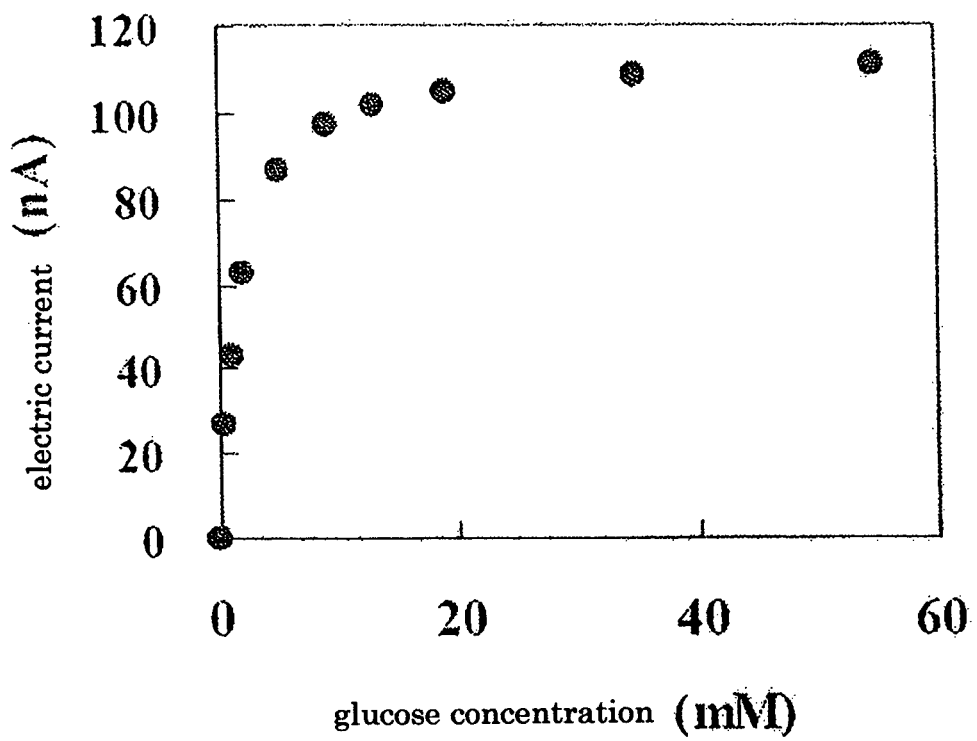
FIG. 3 shows the correlation between the glucose concentration and the electric current value when Ketchen black was used in the FADGDH enzyme immobilized layer and the carbon paste was used in the electrode material.

To KB (100 mg), Milli Q water (400 μl) and 5 Nafion (1-propanol 48% aqueous solution) (1 ml) were added. The mixture was mixed well and left to stand for 3 days to provide a KB ink. A mixture of 100 mM p.p.b. (pH 7.0) (10 μl) and 8.4 U/ml FADGDH (40 μl) with the KB ink (10 μl) was used as an FADGDH/KB ink. To an integral electrode (φ0.4 mm) filled with carbon paste (CP) as an electrode material, the FADGDH/KB ink was added dropwise so as to obtain 25 U/mm² and dried at 4° C. for 2 hours. FIG. 3 shows the correlation between the steady-state electric current value and the glucose concentration in the reaction solution. As shown in FIG. 3, in the case of the present enzyme, the electric current value at 55 mM was about 110 nA even though the same area of the electrode and the same amount of the enzyme were used. The current density of the present enzyme electrode at 5 mM glucose was 690 nA/mm².

Comparative Example 2

Figure 4:
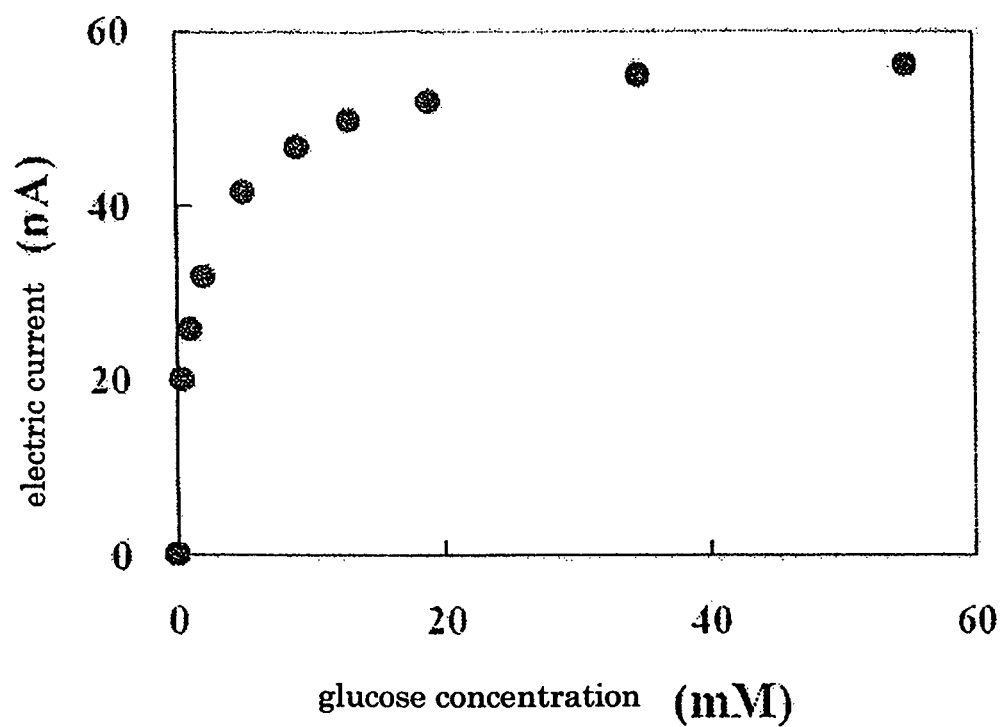
FIG. 4 shows the correlation between the glucose concentration and the electric current value when the carbon paste was used in the FADGDH enzyme immobilized layer and the carbon paste was used in the electrode material.

An enzyme electrode was prepared in the same procedures as described in Example 1 except that carbon paste (hereinafter referred to as CP) having a particle diameter of 7000 nm and a specific surface area of 1 m²/g, instead of KB, was used as a carbon particle. To CP (100 mg), Milli Q water (400 μl) and 5% Nafion (1-propanol 48% aqueous solution) (1 ml) were added. The mixture was mixed well and left to stand for 3 days to provide a CP ink. A mixture of 100 mM p.p.b. (pH 7.0) (10 μl) and 8.4 U/ml FADGDH (40 μl) with the CP ink (10 μl) was used as an FADGDH/CP ink. To an integral electrode (φ0.4 mm) filled with CP as an electrode material, the FADGDH/CP ink was added dropwise so as to attain 25 U/mm² and dried at 4° C. for 2 hours. FIG. 4 shows the correlation between the steady-state electric current value and the glucose concentration in the reaction solution. As shown in FIG. 4, in the case of the FADGDH+CP electrode, the electric current value at 55 mM was about 55 nA even though the same area of the electrode and the same amount of the enzyme were used. The current density of the present enzyme electrode at 5 mM glucose was 330 nA/mm².

It was confirmed that, by comparing FIG. 3 and FIG. 4, in cases where the integral electrode filled with the same CP as an electrode layer was used, the response current value decreased from 690 nA to about 55 nA by changing the ink material, with which this electrode is coated, from the FADGDH/KB ink to the FADGDH/CP ink. That is, it was confirmed that, when the same electrode layer was used, the smaller the particle diameter of the carbon particle on which the enzyme was supported was and the larger the specific surface area thereof was, the higher the respond current became.

Example 3

In order to examine an influence of the specific surface area of a carbon particle on which an enzyme is supported using the same glassy carbon (GC) electrode as an electrode layer, a response current was measured, using as the carbon particle, in addition to the KB used above, VULCAN (VC, a trademark of Cabot) having a particle diameter of 30 nm and a specific surface area of 254 m²/g, Lion Paste (LP, a trademark of Lion Corporation) which is a paste composed of acetylene black (Denka Black, DB, Denki Kagaku Kogyo Kabushiki Kaisha) having a particle diameter of 35 nm and a specific surface area of 68 m²/g and KB.

First, to KB (100 mg), Milli Q (200 µl) and 5% Nafion (1200 µl) were mixed to provide a KB ink. To VC (100 mg), Milli Q (200 µl) and 5% Nafion (1200 µl) were mixed to provide to a VC ink. The KB ink and VC ink, 100 mM p.p.b. (pH 7.0) and 4.6 U/µl FADGDH were mixed at a volume ratio of 1:3.8:3.2 to provide a KB enzyme ink and VC enzyme ink, respectively. Next, to DB (50 mg), Milli Q (850 µl) and 5% Nafion (600 µl) were mixed to provide a DB ink. The DB ink, 100 mM p.p.b. (pH 7.0) and 4.6 U/µl FADGDH were mixed at a volume ratio of 1:1.4:1.6 to provide a DB enzyme ink. Also, using Lion Paste with KB as a major component, Lion Paste W-311N, 5% Nafion, 100 mM p.p.b. (pH 7.0) and 4.6 U/µl FADGDH were mixed at a volume ratio of 1:1:4:4 to provide LP enzyme ink. Further, without using a carbon particle(s), 5% Nafion, 100 mM p.p.b. (pH 7.0) and 4.6 U/µl FADGDH were mixed at a volume ratio of 1:5:4 to provide an enzyme ink.

The KB enzyme ink (KBink in FIG. 5), VC enzyme ink (VCink in FIG. 5), DB enzyme ink (DBink in FIG. 5), Lion Paste enzyme ink (LPink in FIG. 5) or enzyme ink (ink in FIG. 5) (5 µl) was added dropwise to a polished glassy carbon (GC) electrode (φ3 mm) and dried at 4° C. for 2 hours. This electrode was subjected to a cross-linking treatment using vapors of 25% glutaraldehyde solution for 30 minutes and then was immersed in 10 mM Tris-HCl (pH 7.0) for 20 minutes. This electrode was immersed in 100 mM p.p.b. (pH 7.0) at 4° C. overnight to be equilibrated. In a three electrode system using the prepared enzyme electrode as a working electrode, Pt as a counter electrode and Ag/AgCl as a reference electrode, as well as using 100 mM p.p.b. (pH 7.0) (10 ml) as a reaction solution, a response current value upon addition of glucose when an electric potential was applied at +250 mV vs. Ag/AgCl was measured and a calibration curve was prepared (150 rpm, 37° C.).

Figure 5:
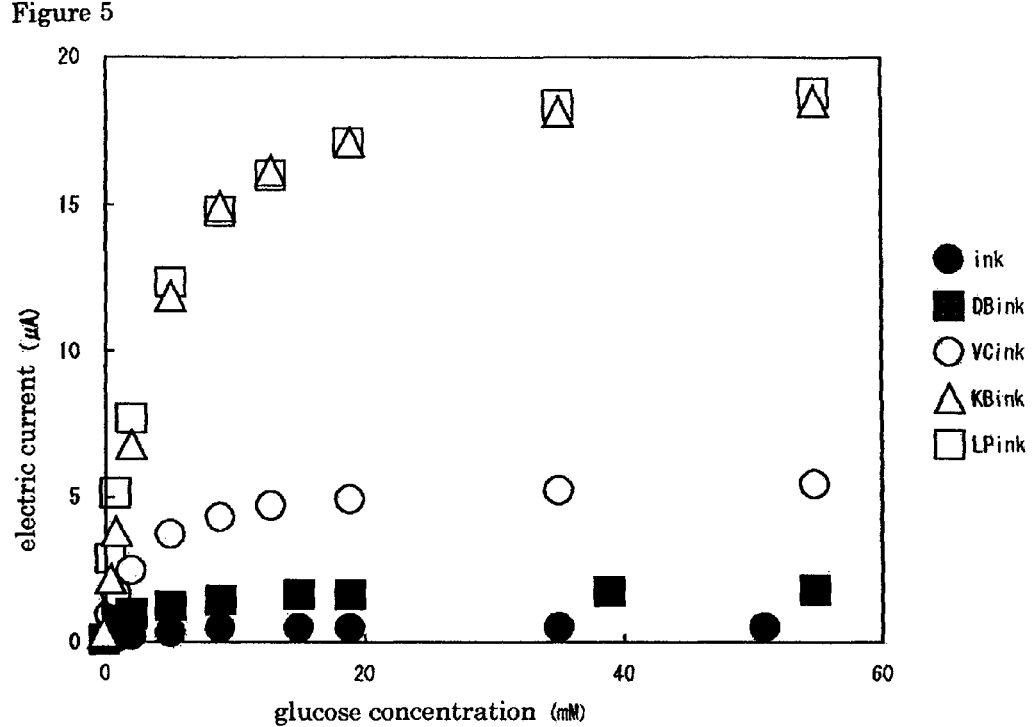
FIG. 5 shows the correlation between the glucose concentration and the electric current value when Ketchen black, Lion Paste, VULCAN and Denka Black were used in the FADGDH enzyme immobilized layer and the glassy carbon was used in the electrode material.
Figure 6:
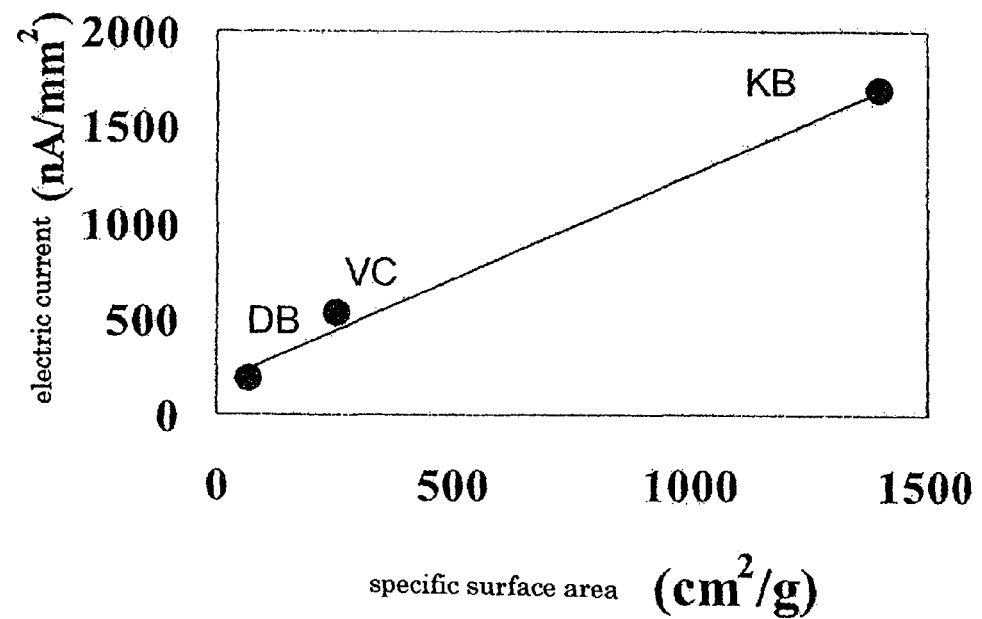
FIG. 6 shows the correlation between the specific surface area of the carbon particle of the enzyme immobilized layer and the response current value.

The results of the measurements of glucose using the thus obtained enzyme electrode are shown in FIG. 5. As the glucose concentration increased, an increase in the electric current was observed in any of the enzyme electrodes. Among them, when the KB enzyme ink or Lion Paste enzyme ink were used, the similar response was obtained, the response being outstandingly high as compared with those of other inks. When the VC enzyme ink was used, the response high enough to be practically acceptable was obtained, while it was lower than those of two inks above. In contrast, when the DB enzyme ink was used, only a signal as low as that in the case of using the enzyme ink without carbon particles was obtained. The correlation between the response current value of these sensors at 5 mM of glucose concentration and the specific surface area of the carbon particle of the ink used is shown in FIG. 6. With VULCAN (VC) having a specific surface area of 254 m²/g, the virtually satisfactory response current was obtained, while with the acetylene black having specific surface area 68 m²/g, the satisfactory response current was not obtained. Thus, it was shown that there was a high correlation between the response current value and the specific surface area of the carbon particle to be used, and the carbon particle having a specific surface area of at least 200 m²/g was required to be used. Also, the particle diameter was all required to be not more than 100 nm.

Example 4

Nafion (5%), Lion Paste W-311N or W-370C, 100 mM p.p.b. (pH 7.0) and 8.4 U/µl ADGDH were mixed at a volume ratio of 1:1:4:4 to provide an enzyme ink. Each of the enzyme inks was added dropwise to a polished glassy carbon (GC) electrode (φ3 mm) such that the amount of FADGDH was 17 U (2.4 U/mm²) and dried at 4° C. for 2 hours. This electrode was subjected to a cross-linking treatment using vapors of 25% glutaraldehyde solution for 30 minutes and then was immersed in 10 mM Tris-HCl (pH 7.0) at room temperature for 20 minutes to remove unreacted glutaraldehyde. This electrode was further immersed in 100 mM p.p.b. (pH 7.0) for 30 minutes to be equilibrated. Using these as a working electrode, a platinum wire as a counter electrode and an Ag/AgCl reference electrode as a reference electrode, as well as using 100 mM p.p.b. (pH 7.0) (10 ml) as a reaction solution, a response current value upon addition of glucose when an electric potential was applied at +250 mV vs. Ag/AgCl was measured. The measurement was carried out at 37° C. while the reaction solution was being stirred at 250 rpm. The response current value was defined as the difference obtained by subtracting the steady-state electric current value obtained at 0 mM glucose from the steady-state electric value measured at each glucose concentration.

Figure 7:
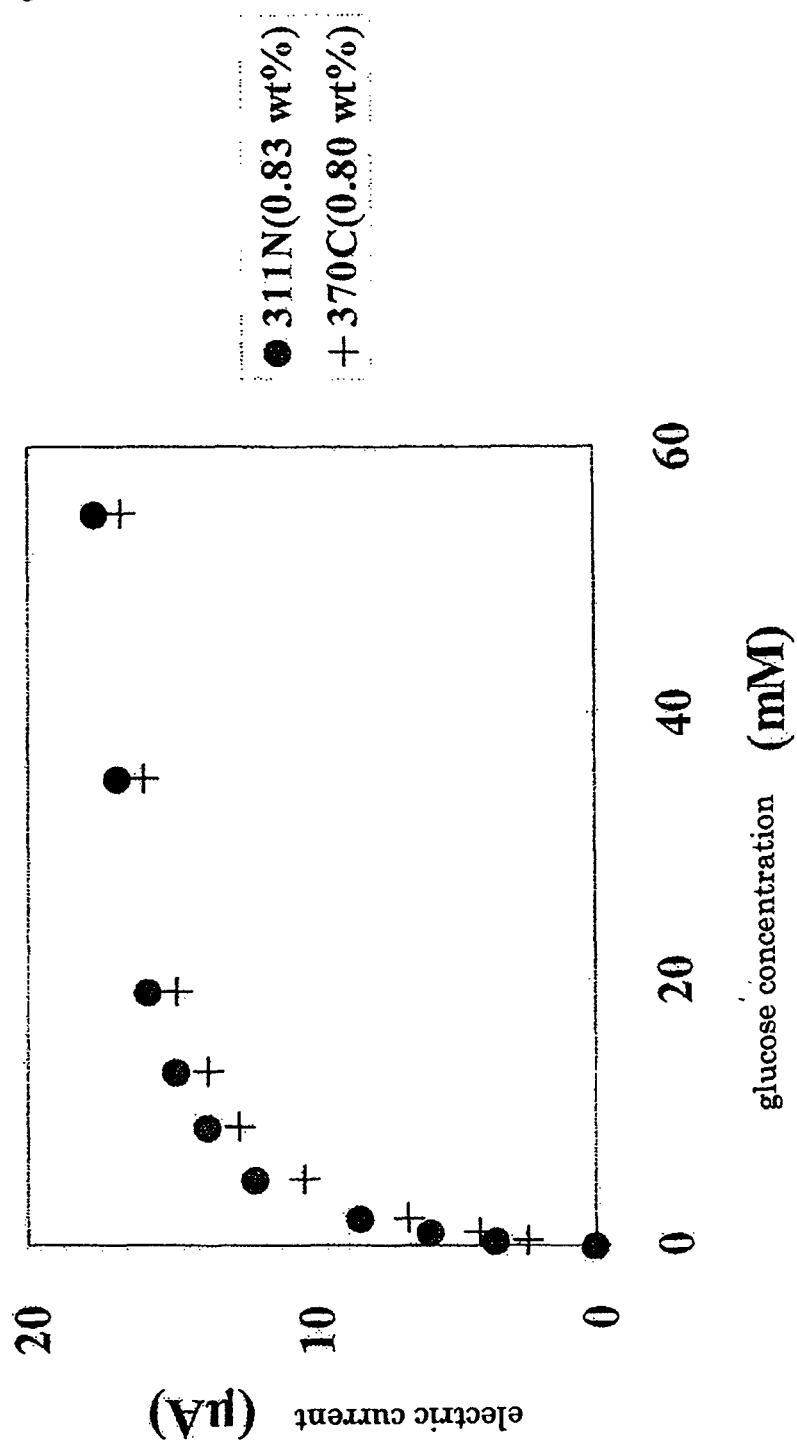
FIG. 7 shows the correlation between the glucose concentration and the electric current value when Lion Paste (W-311N, W-370) was used in the FADGDH enzyme immobilized layer and the glassy carbon was used in the electrode material.

The results of the measurements of glucose using the thus obtained enzyme electrode are shown in FIG. 7. As the glucose concentration increased, an increase in the electric current was observed. When Lion Paste W-311N or W-370C was used as a carbon particle used in an enzyme layer, the current density observed at 5 mM of glucose concentration was 1684 nA/mm² or 1452 nA/mm², respectively. It was confirmed that, when Lion Paste having KB as a major component was used, the high response current was obtained regardless of the types of products.

Example 5

As a carbon particle, VULCAN (VC) having a particle diameter of 30 nm and a specific surface area of 254 m²/g was provided. To VC (100 mg), Milli Q water (400 µl) and 5% Nafion (1-propanol 48% aqueous solution) (1 ml) were added. The mixture was mixed well and left to stand for 3 days to provide a VC ink. A mixture of 100 mM p.p.b. (pH 7.0) (10 µl) and 8.4 U/ml FADGDH (40 µl) with the VC ink (10 µl) was used as an FADGDH/VUL ink. To an integral electrode (φ0.75 mm) filled with VC as an electrode material, the FADGDHNC ink was added dropwise so as to attain 25 U/mm² and dried at 4° C. for 2 hours. The prepared enzyme electrode was used as a working electrode, Pt was used as a counter electrode, and an Ag/AgCl reference electrode was used as a reference electrode. FIG. 5 shows the results of measurements of a response current value upon addition of glucose when an electric potential was applied at +250 mV vs. Ag/AgCl using 100 mM p.p.b. (pH 7.0) (10 ml) as a reaction solution in a three electrode system. The measurement was carried out at 37° C. while the reaction solution was being stirred at 250 rpm. The response current value was defined as the difference obtained by subtracting the electric current value obtained at 0 mM glucose from the electric value measured at each glucose concentration.

Figure 8:
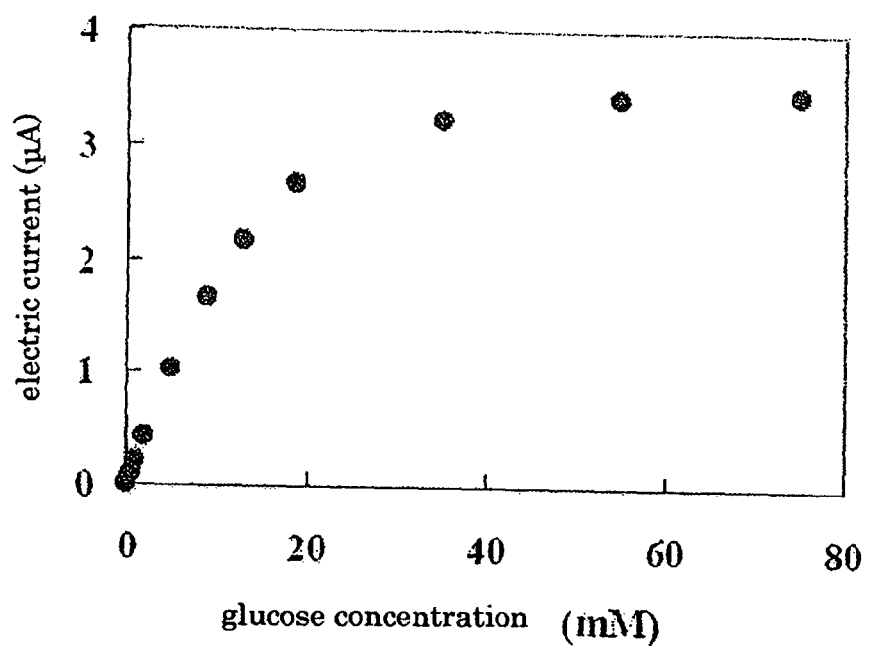
FIG. 8 shows the correlation between the glucose concentration and the electric current value when VULCAN was used in the FADGDH enzyme immobilized layer and VULCAN was used in the electrode material.

As shown in FIG. 8, by gradually increasing the glucose concentration, the observed electric current value increased. At a final glucose concentration of 55 mM, the response current value was at about 3500 nA. At 5 mM glucose, the current density was 2327 nA/mm$^2$. As described above, it was confirmed that, in the VC ink using VC having a particle diameter of 30 nm and a specific surface area of 254 m$^2$/g, the satisfactory response current value was obtained either when a glassy carbon was used for the electrode layer as shown in Example 3 or when VC was used for the electrode layer as shown in the present example.

As described above, it was confirmed that when the carbon particle was used for both the electrode layer and enzyme layer, if the same type of carbon particle was used in the electrode layer, the smaller the particle diameter of the carbon particle used in the enzyme layer was and the larger the specific surface area thereof was, the higher the response current became, and particularly when the carbon particle having a particle diameter of not more than 100 nm and a specific surface area of at least 200 m$^2$/g was used, a satisfactory response current was obtained. And, it was also confirmed that if the same type of carbon particle was used in the enzyme layer, the smaller the particle diameter of the carbon particle used in the electrode layer was and the larger the specific surface area thereof was, the higher the response current became, and particularly when the carbon particle having a particle diameter of not more than 100 nm and a specific surface area of at least 200 m$^2$/g was used, the response current was improved.

Examples in the Case of Using Metal Wire as Electrode Layer

Next, examples in the case of using a metal wire as an electrode layer and using an LP ink as an enzyme layer will be described below.

Example 6

A gold wire ($\phi$0.5 mm) was immersed with a piranha solution (hydrogen peroxide: concentrated sulfuric acid=1:3) for 5 minutes to be washed, which was repeated 3 times. This gold wire was coated with an enzyme ink prepared using Lion Paste W-311N under the same conditions as described in the explanation of Example 4 and dried at 4° C. for 2 hours. This electrode was subjected to a cross-linking treatment in the same manner as described in the explanation of Example 4 to be equilibrated, and then used as a working electrode. In a three electrode system using a gold wire with no coatings as a counter electrode and an Ag/AgCl reference electrode as a reference electrode, a response current value upon addition of glucose was measured in the same manner as described in the explanation of Example 4.

Figure 9:
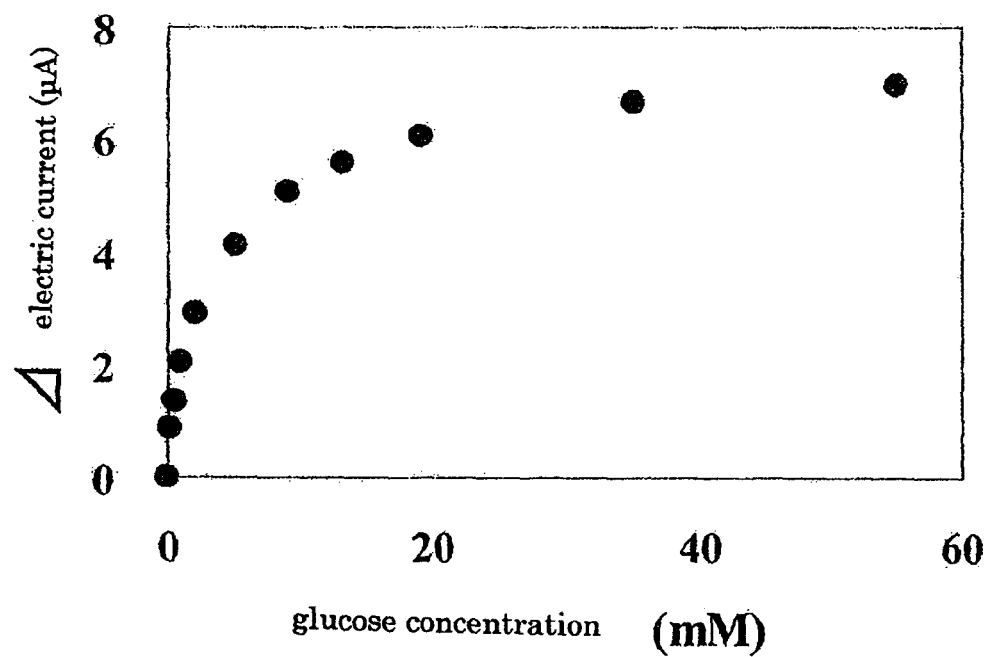
FIG. 9 shows the correlation between the glucose concentration and the electric current value when Lion Paste (W-311N) was used in the FADGDH enzyme immobilized layer and the gold wire was used in the electrode material.

The results of the measurements of glucose using the thus obtained enzyme electrode are shown in FIG. 9. As the glucose concentration increased, an increase in the electric current was observed. The current density observed at 5 mM of glucose concentration was 201 nA/mm$^2$.

Example 7

Nafion (5%), Lion Paste W-311N, 100 mM p.p.b. (pH 7.0) and 8.4 U/μl FADGDH were mixed at a volume ratio of 1:1:4:4 to provide an enzyme ink. With the enzyme ink, 10 mm of the end of a stainless wire ($\phi$0.5 mm) was coated and dried at 4° C. for 2 hours. This stainless wire was subjected to a cross-linking treatment using vapors of 25% glutaraldehyde solution for 30 minutes and then was immersed in 10 mM (pH 7.0) at room temperature for 20 minutes to remove unreacted glutaraldehyde. This stainless wire was further immersed in 100 mM p.p.b. (pH 7.0) for 1 hour to be equilibrated. Using this as a working electrode, a platinum wire as a counter electrode, Ag/AgCl as a reference electrode, as well as using 100 mM p.p.b. (pH 7.0) (10 ml) as a reaction solution, a response current value upon addition of glucose when an electric potential was applied at +400 mV vs. Ag/AgCl was measured. The measurement was carried out at 37° C. while the reaction solution was being stirred at 250 rpm. The response current value was defined as the difference obtained by subtracting the steady-state electric current value obtained at 0 mM glucose from the steady-state electric value measured at each glucose concentration.

Figure 10:
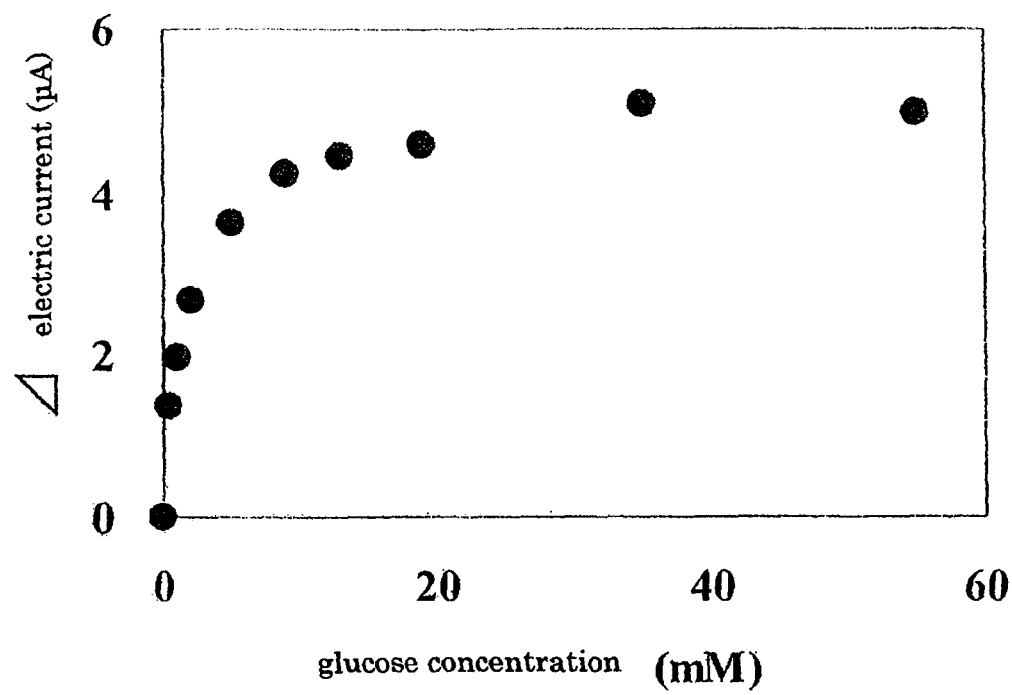
FIG. 10 shows the correlation between the glucose concentration and the electric current value when Lion Paste (W-311N) was used in the FADGDH enzyme immobilized layer and the stainless wire was used in the electrode material.

The response current values upon addition of glucose when each stainless wire on which the enzyme was immobilized was used as the working electrode are shown in FIG. 10. As the glucose concentration increased, an increase in the electric current was observed. The current density observed at 5 mM of glucose concentration was 232 nA/mm$^2$.

Example 8

A stainless portion (0.165 mm$^2$) of the end of a stainless integral electrode was used as a working electrode and the other stainless portion (0.942 mm$^2$) was used as a counter electrode. The working electrode was immersed in an enzyme ink in which 5% Nafion, Lion Paste W-311N, 100 mM p.p.b. (pH 7.0) and 8.4 U/μl FADGDH were mixed at a volume ratio of 1:1:4:4 and then dried at 4° C. for 2 hours. This electrode was subjected to a cross-linking treatment using vapors of 25% glutaraldehyde solution for 30 minutes and was then immersed in 100 mM p.p.b. (pH 7.0) for 30 minutes to be equilibrated. In a three electrode system using a potentiostat with this electrode as well as using Ag/AgCl as a reference electrode, a response current value upon addition of glucose when an electric potential was applied at +400 mV vs. Ag/AgCl was measured. The measurement was carried out, using 100 mM p.p.b. (pH 7.0) (10 ml) as a reaction solution, at 37° C. and a stirring rate of 150 rpm. The response current value was defined as the difference obtained by subtracting the steady-state electric current value obtained at 0 mM glucose from the steady-state electric current value measured at each glucose concentration.

Figure 11:
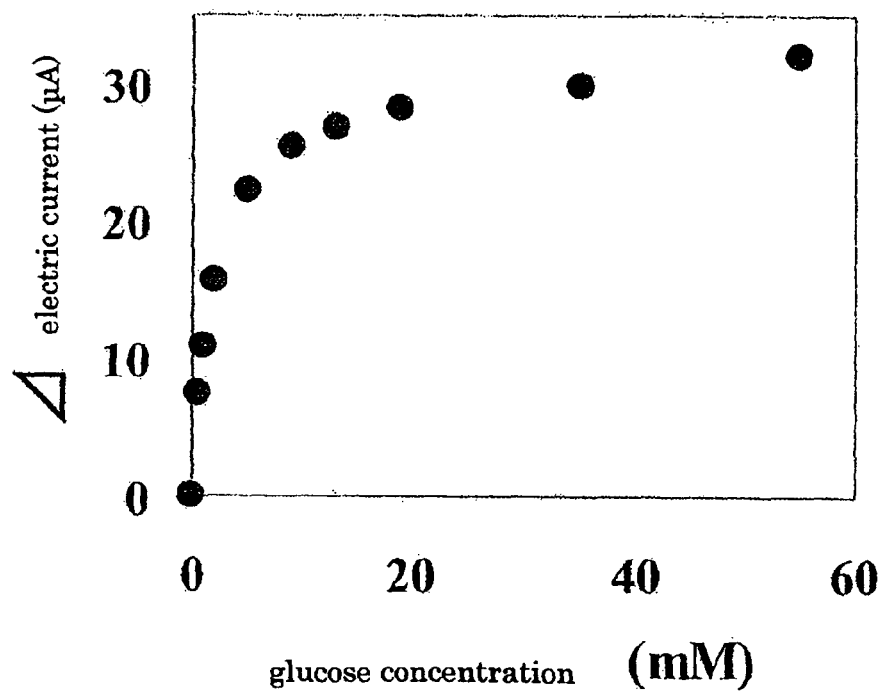
FIG. 11 shows the correlation between the glucose concentration and the electric current value when Lion Paste (W-311N) was used in the FADGDH enzyme immobilized layer and the stainless integral electrode was used in the electrode material.

A calibration curve of the response current value of the prepared stainless integral electrode against glucose is shown in FIG. 11. In the measurement in an electrode system, the response current value at 5 mM of glucose concentration was 134 nA/mm$^2$. This value was almost the same as the value obtained from the enzyme electrode of Example 7 prepared using the stainless wire of 0.5 mm. Thus, a glucose sensor using this stainless integral electrode was constructed.

Example of Preparation of Enzyme Electrode

Example 9

Figure 12:
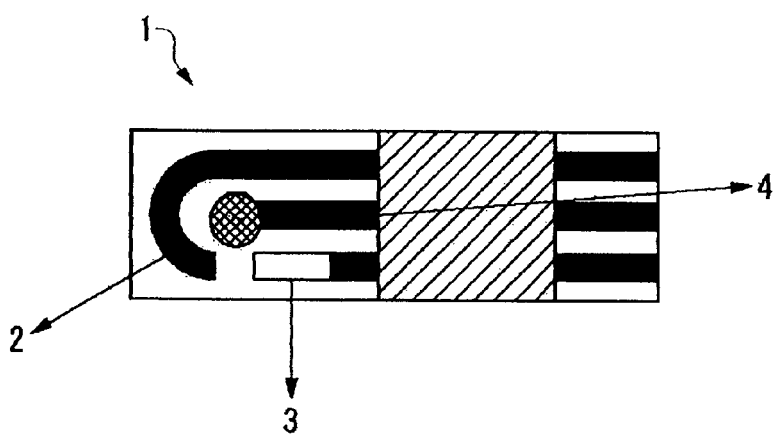
FIG. 12 shows a commercially available electrode made by supporting carbon particles on the polymer substrate.

An enzyme ink was coated on a commercially available electrode (Bio Device Technology Co., Ltd., DepChip circular-type carbon electrode) (shown in FIG. 12) which is prepared by supporting carbon particles on a polymer substrate, thereby constructing an enzyme electrode. As the enzyme ink, a mixture of 5% Nafion, Lion Paste W-311N, 100 mM p.p.b. (pH 7.0) and 4.0 U/µl FADGDH at a volume ratio of 1:1:1:7 was used. This enzyme ink (1.5 µl) was coated on the electrode of FIG. 12 and then dried at 4° C. for 2 hours. In a three electrode system using a potentiostat with this electrode as well as using Ag/AgCl on the same electrode as a reference electrode, a response current value upon addition of glucose when an electric potential was applied at +250 mV vs. Ag/AgCl was measured.

Figure 13:
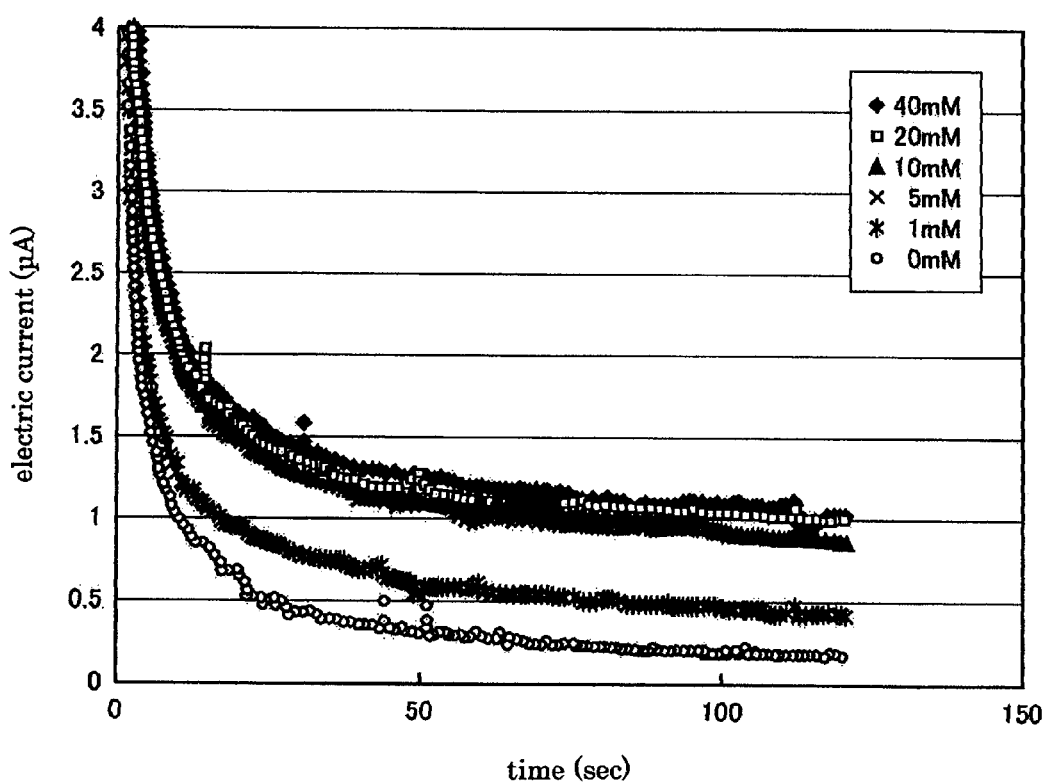
FIG. 13 shows a response curve after the samples containing glucose were added dropwise to the enzyme electrode made by coating the enzyme ink on the electrode shown in FIG. 12 and the electric potential was applied.
Figure 14:
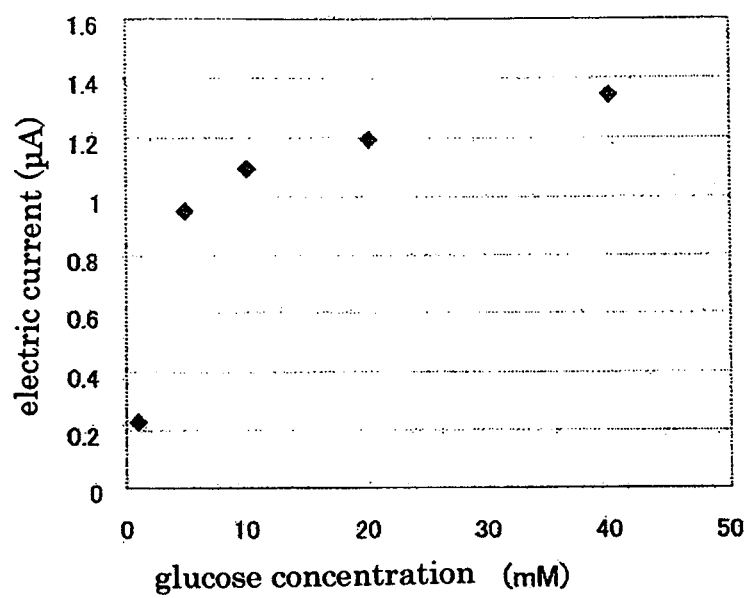
FIG. 14 shows, in the response curve shown in FIG. 13, the correlation between the glucose concentration in the sample and the electric current value at 5 seconds after the application of the electric potential.

In the measurement, a sample solution (5 µl) containing various concentrations of glucose dissolved in 100 mM p.p.b. (pH 7.0) was first added dropwise to the enzyme electrode under conditions of no electric potentials being applied to the electrode. And, 5 seconds later, in a three electrode system using a potentiostat as well as using Ag/AgCl on the same electrode as a reference electrode, an electric potential was applied at +250 mV vs. Ag/AgCl. Changes of the electric current value observed when the samples containing various concentrations were added are shown in FIG. 13. As shown, the observed electric current value varies depending on the added glucose concentration. Using the electric current value at 5 seconds after the application of the electric potential as an index, the correlation with the glucose concentration was examined. A graph taking the electric current value at 5 seconds after the application of the electric potential along vertical axis and taking the glucose concentration in the sample along horizontal axis is shown in FIG. 14. As described herein, using the present enzyme electrode, without adding an electron mediator, the glucose concentration was measured.

The examples above are merely illustrative of the present invention. Hence, needless to say, even with materials and conditions other than those shown in the examples herein, as long as they are included within the claims of the present invention, the same effects are to be obtained, and also other various alterations, modifications and the like are possible. For instance, the enzyme electrode using the ink material according to the present invention, as described in detail, can be used as a working electrode in a glucose sensor and can preferably be applied to an anode enzyme in a fuel cell using glucose as fuel.

What is claimed is:

1. An enzyme electrode comprising an enzyme layer comprising carbon particles having a particle diameter of not more than 100 nm and a specific surface area of at least 200 $m^2/g$ carrying glucose dehydrogenase (GDH) with flavine adenine dinucleotide (FAD) as a coenzyme; and a single electrode material consisting only of carbon particles having a particle diameter of not more than 100 nm and a specific surface area of at least 200 $m^2/g$ contacting said enzyme layer, wherein the enzyme electrode does not include an electron mediator.

2. The enzyme electrode according to claim 1, wherein the glucose dehydrogenase (GDH) is an oxidoreductase catalytic subunit or a complex of an oxidoreductase catalytic subunit and an electron transfer subunit.

3. A glucose sensor using the enzyme electrode according to claim 1.

4. The enzyme electrode according to claim 1, wherein the carbon particle has a particle diameter of 30-34 nm and a specific surface area of 254-1400 $m^2/g$.

5. An enzyme fuel cell using the enzyme electrode according to claim 1.

6. The enzyme fuel cell according to claim 5, wherein the enzyme electrode is used as the anode.

7. A method for producing an enzyme electrode, comprising: coating a surface of an electrode layer comprising a single electrode material consisting of carbon particles having a particle diameter of not more than 100 nm and a specific surface area of at least 200 $m^2/g$ with an ink material wherein the ink material comprises carbon particles having a particle diameter of not more than 100 nm and a specific surface area of at least 200 $m^2/g$ and glucose dehydrogenase (GDH) with flavine adenine dinucleotide (FAD) as a coenzyme; and then drying the coating, wherein the enzyme electrode does not include an electron mediator.

8. The method for producing an enzyme electrode according to claim 7, further comprising adding a solid polyelectrolyte to an enzyme film in which the enzyme is absorbed, or coated and dried.

9. The method for producing an enzyme electrode according to claim 7, wherein the ink material further comprises a solid polyelectrolyte.

10. The method for producing an enzyme electrode according to claim 7, wherein the glucose dehydrogenase (GDH) is an oxidoreductase catalytic subunit or a complex of an oxidoreductase catalytic subunit and an electron transfer subunit.

11. The method for producing an enzyme electrode according to claim 7, wherein the carbon particle has a particle diameter of 30-34 nm and a specific surface area of 254-1400 $m^2/g$.

* * * * *

UNITED STATES PATENT AND TRADEMARK OFFICE
CERTIFICATE OF CORRECTION

PATENT NO. : 9,617,576 B2
APPLICATION NO. : 12/678268
DATED : April 11, 2017
INVENTOR(S) : Wakako Tsugawa et al.

Page 1 of 1

It is certified that error appears in the above-identified patent and that said Letters Patent is hereby corrected as shown below:

On the Title Page

Item (57), (Abstract) at Line 4, Change "flavine" to --flavin--.

In the Specification

In Column 1 at Line 67, After "from" delete "a".

In Column 2 at Line 54, After "attained" insert --.--.

In Column 3 at Line 4, Change "flavine" to --flavin--.

In Column 3 at Line 21, Change "flavine" to --flavin--.

In Column 3 at Line 33, Change "flavine" to --flavin--.

In Column 3 at Line 48, Change "flavine" to --flavin--.

In Column 4 at Line 29, Change "flavine" to --flavin--.

In Column 4 at Line 59, Change "a" to --α--.

In Column 11 at Line 41, Change "sulfric" to --sulfuric--.

In the Claims

In Column 13 at Line 45, In Claim 1, change "flavine" to --flavin--.

In Column 14 at Line 27, In Claim 7, change "flavine" to --flavin--.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*